United States Patent
Pan et al.

(10) Patent No.: US 10,828,515 B2
(45) Date of Patent: Nov. 10, 2020

(54) COMPOSITIONS CONTAINING PHENOLIC COMPOUNDS HAVING SYNERGISTIC ANTIOXIDANT BENEFITS

(71) Applicant: L'OREAL, Paris (FR)

(72) Inventors: Zhi Pan, Clark, NJ (US); Ashleigh Murtaugh, Clark, NJ (US); Fan Hu, Clark, NJ (US)

(73) Assignee: L'OREAL, Paris (FR)

( * ) Notice: Subject to any disclaimer, the term of this patent is extended or adjusted under 35 U.S.C. 154(b) by 444 days.

(21) Appl. No.: 15/339,036

(22) Filed: Oct. 31, 2016

(65) Prior Publication Data

US 2018/0116950 A1    May 3, 2018

(51) Int. Cl.
| | |
|---|---|
| *A61K 8/9789* | (2017.01) |
| *A61Q 19/08* | (2006.01) |
| *A61K 8/67* | (2006.01) |
| *A61K 8/49* | (2006.01) |

(52) U.S. Cl.
CPC .............. *A61Q 19/08* (2013.01); *A61K 8/498* (2013.01); *A61K 8/678* (2013.01); *A61K 8/9789* (2017.08); *A61K 2800/522* (2013.01); *A61K 2800/5922* (2013.01)

(58) Field of Classification Search
None
See application file for complete search history.

(56) References Cited

U.S. PATENT DOCUMENTS

| | | |
|---|---|---|
| 5,824,320 A | 10/1998 | Rouillard et al. |
| 9,072,919 B2 | 7/2015 | Pan et al. |
| 2006/0018867 A1* | 1/2006 | Kawasaki .............. A61K 8/898 424/70.122 |
| 2009/0162304 A1* | 6/2009 | DiLeva .................. A61K 8/678 424/62 |

FOREIGN PATENT DOCUMENTS

WO    2014075866 A2    5/2014

OTHER PUBLICATIONS 2018 https://www.verywellhealth.com/the-benefits-of-coptis-chinensis-88938.*

* cited by examiner

*Primary Examiner* — Terry A McKelvey
*Assistant Examiner* — Catheryne Chen
(74) *Attorney, Agent, or Firm* — McNees Wallace & Nurick LLC

(57) ABSTRACT

Compositions comprising at least one polyphenol selected from the group consisting of *Silybum Marianum* extract, *Origanum Vulgare* leaf extract, and *Coptis Chinensis* root extract, and baicalin, and Vitamin E, all present in amounts sufficient to produce synergistic antioxidant activity and provided for cosmetic and other uses.

20 Claims, No Drawings

COMPOSITIONS CONTAINING PHENOLIC COMPOUNDS HAVING SYNERGISTIC ANTIOXIDANT BENEFITS

BACKGROUND OF THE INVENTION

The formation of free radicals is widely considered to play a significant role in the mechanisms of skin aging. Free radicals are highly reactive molecules with unpaired electrons that can directly damage various cellular membranes, lipids, proteins, RNA and DNA. The damaging effects of these reactive oxygen species are induced inside the tissue and cells during normal metabolism and externally through various oxidative stresses. UV exposure and environmental pollution can accelerate skin aging by producing free radicals in skin. Antioxidants protect cells from the damage of oxidative stress by scavenging free radicals and inhibiting oxidation reactions. The topical application of antioxidants is broadly used in skin care products to prevent skin aging. It has been previously shown in the cosmetic related fields that polyphenols act synergistically with other antioxidants such as Vitamin E and carotenoids.

While there are some examples of antioxidants that can provide protective benefits, there remains a need for compositions that offer enhanced options for protective formulations, particularly in the cosmetics arts.

BRIEF SUMMARY OF THE INVENTION

The invention provides compositions comprising (a) baicalin, (b) at least one additional polyphenol, and (c) Vitamin E, present in the compositions in amounts sufficient to produce synergistic antioxidant activity.

The compositions can also contain additional antioxidants. The invention thus also provides compositions comprising (a) baicalin, (b) at least one additional polyphenol, (c) Vitamin E, and (d) one or more additional antioxidant different than (a) and (b), wherein the components (a)® (c) are present in amounts sufficient to produce synergistic antioxidant activity.

In addition to the Vitamin E and baicalin, the at least one additional polyphenol can include one or more of *Silybum Marianum* extract, *Origanum Vulgare* leaf extract, and *Coptis Chinensis* root extract (or other plant extracts composed with different purity of berberine or its derivatives).

In accordance with some embodiments, the compositions include (a) about 0.01% to about 20% of at least one polyphenol selected from the group consisting of *Silybum Marianum* extract, *Origanum Vulgare* leaf extract, and *Coptis Chinensis* root extract, (b) about 0.01% to about 20% of baicalin; and (c) about 0.01% to about 20% of Vitamin E, all amounts present as percentages by weight based on the total weight of the composition.

In accordance with some embodiments, the compositions include (a) about at least 0.5% of at least one polyphenol selected from the group consisting of *Silybum Marianum* extract, *Origanum Vulgare* leaf extract, and *Coptis Chinensis* root extract, (b) about at least 0.5% of baicalin; and (c) about at least 1% of Vitamin E, all amounts present as percentages by weight based on the total weight of the composition.

In accordance with some embodiments, the compositions include (a) about 0.5% of at least one polyphenol selected from the group consisting of *Silybum Marianum* extract, *Origanum Vulgare* leaf extract, and *Coptis Chinensis* root extract, (b) about 0.5% of baicalin; and (c) about 1% of Vitamin E, all amounts present as percentages by weight based on the total weight of the composition.

The compositions can optionally contain at least one hydrotrope, such as caffeine or nicotinamide that is acceptable for use in cosmetic compositions, and/or at least one glycol.

Another aspect of the invention provides methods for preparing an composition, the method comprising the step of including in the composition (a) baicalin, (b) at least one additional polyphenol, and (c) Vitamin E in amounts sufficient to produce synergistic antioxidant activity.

A further aspect of the invention provides methods for preparing an composition, the method comprising the step of including in said composition (d) one or more additional antioxidants different than (a)-(c), and a hydrotrope (e).

A further aspect of the invention provides methods for preparing an cosmetic formulation comprising an aqueous antioxidant composition, the method comprising the step of including in said formulation one or more components for forming one of an aqueous serum, an oil-in-water emulsion, and a water-in-oil emulsion.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The term "comprising" (and its grammatical variations) as used herein is used in the inclusive sense of "having" or "including" and not in the exclusive sense of the terms "consisting only of," "consisting essentially of" and "consisting of."

"W/O emulsion," and "W/Si emulsion" as used herein, includes a water phase dispersed in an oil phase, where the oil phase is a continuous phase and includes at least one Si emulsifier.

"Cosmetically acceptable" means compatible with any keratinous substrate. For example, "cosmetically acceptable carrier" means a carrier that is compatible with any keratinous substrate.

The present invention provides compositions comprising (a) baicalin, (b) at least one additional polyphenol, and (c) Vitamin E, wherein the baicalin (a) polyphenol (b) and Vitamin E (c) are present in amounts sufficient to produce synergistic antioxidant activity.

Applicants have surprisingly found and provide evidence in this disclosure that the antioxidant capacities of certain polyphenolic compounds in combination with baicalin and Vitamin E, are dramatically stronger than the additive effects of the individual compounds. This surprising synergistic antioxidant effect in combination with the other known benefits of the compounds individually, can be employed advantageously in cosmetic compositions, particularly for photo protection and oily skin and acne applications. Components and the compositions are more fully described herein below, as are other optional components useful in cosmetic formulations.

The compositions may also contain additional antioxidants, hydrotropes, additives and other components, as described herein below.

Individual components were evaluated for antioxidant activity individually, and in combination, and the results are as presented in the Examples below. Presuming the antioxidant effects would be additive, predictions were made for the combinations and are shown in comparison to the actual activity measured for the inventive combinations in Table 2. Strong synergistic effects were observed only in combinations that included baicalin, at least one additional polyphenol, and Vitamin E as shown in sample 2, 3 and 4 in the Examples. There is no synergistic effect in samples of a non-baicalin containing polyphenol and Vitamin E. Likewise, when another flavonoid compound, polydatin (a natural precursor of resveratrol) was used in place of certain polyphenols, with baicalin and Vitamin E, only an extremely modest synergy was observed. Since these tests were performed on water-based solutions, identified associations between baicalin, certain polyphenols, and Vitamin E are ready to be applied in any cosmetic product to provide a stronger protection from free radicals.

The compositions can also contain additional antioxidants. The invention thus also provides compositions comprising (a) baicalin, (b) at least one additional polyphenol, (c) Vitamin E, and (d) one or more additional antioxidant different than (a) and (b), wherein the components (a)-(c) are present in amounts sufficient to produce synergistic antioxidant activity.

The compositions provide stronger protective effects against free radicals and the damaging effects of reactive oxygen species in that the combinations in the compositions herein show synergistic antioxidant activity wherein the activity of an inventive composition is greater than the sum (addition) of the antioxidant activity of each of the components individually.

Synergism was determined by comparing the antioxidant capacities of combinations of components measured by oxygen radical absorbance capacity assay (ORAC) with expected or additive values of the individual compounds. As reflected in the Examples below, the expected ORAC is the combined (additive) antioxidant capacity of each individual antioxidant compound in the association, measured individually and assuming that each is functioning independently. The expected ORAC value of a certain association can be calculated by using the following equation: ORAC (total)=sum of ORAC (compound n, individually) multiplied by the Percentage (compound n, of use in a cosmetic composition), n=1, 2, 3 . . . . Synergistic antioxidant activity is present when a measured ORAC is significantly larger than the expected value. Significantly larger than the expected value refers to measured ORAC values at least 25% greater than expected values. Some of the compositions as shown in the examples exhibit synergistic antioxidant activity greater than 50%.

The ORAC assay is one of most commonly used methods to evaluate the capacity of antioxidants against ROS (reactive oxygen species), specific for peroxyl which is one of the most important free radicals present in the human skin environment. The ORAC assay measures the oxidative degradation of the fluorescent probe (fluorescein) after being mixed with free radical generators such as azo-initiator compounds (2,2'-Azobis(2-amidinopropane)dihydrochloride, AAPH). Azo-initiators are considered to produce the peroxyl radical by heating, which damages the fluorescent molecule, resulting in the loss of fluorescence. Antioxidants are considered to protect the fluorescent molecule from the oxidative degeneration. By quantifying the decay of fluorescence using a fluorometer, the degree of protection is determined comparing with a standard control antioxidant Trolox. The result is expressed in µMol equivalent of Trolox. Equipment that can automatically measure and calculate the capacity is commercially available, such as the VarioSkan flash microplate reader from Thermo Scientific.

References disclosing ORAC assays include: Cao G, Alessio H, Cutler R (1993). "Oxygen-radical absorbance capacity assay for antioxidants". Free Radic Biol Med 14 (3): 303-11; Ou B, Hampsch-Woodill M, Prior R (2001). "Development and validation of an improved oxygen radical absorbance capacity assay using fluorescein as the fluorescent probe". J Agric Food Chem 49 (10): 4619-26; Huang D, Ou B, Prior R (2005). "The chemistry behind antioxidant capacity assays". J. Agric. Food Chem. 53 (6): 1841-56; and Garrett A R, Murray B K, Robison R A, O'Neill K L (2010). "Measuring antioxidant capacity using the ORAC and TOSC assays". Advanced Protocols in Oxidative Stress II: Methods in Molecular Biology (series), Donald J Armstrong (ed) 594: 251-62.

Phenolic Compounds

Phenolic compounds are a structural class of natural, synthetic, and semisynthetic organic compounds that have one or more phenolic constituents. Phenolic compounds containing multiple phenol groups are known as polyphenols. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Flavonoids are further categorized, according to chemical structure, into chalcones, flavones, flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

Non-flavonoid polyphenols include lignans, aurones, stilbenoids, curcuminoids and other phenylpropanoids. Many of them are also well-known antioxidants like resveratrol, curcumin, and pinoresinol.

Other phenolic compounds, in addition to polyphenols, include alkylphenols, betacyanins, capsacinoids, hydroxybenzoketones, methoxyphenols, naphthoquinones, and phenolic terpenes. Some popular examples are ferulic acid, hydroxytyrosol, cinnamic acid, caffeic acid, and p-coumaric acid.

The at least one phenolic compound is solubilized in the compositions, and the amount of phenolic compound will depend on the specific phenolic compound and the type and amount of hydrotrope present in the compositions.

Isolates and extracts comprising antioxidant compounds of interest such as, but not limited to, baicalin, and other flavonoids, can be obtained containing one or more antioxidant compounds of interest in amounts up to 95% or greater. Thus, in accordance with the various embodiments, an extract comprising antioxidant compounds of interest means and includes an extract consisting of 100% of the compound of interest, as well as extracts comprising from less than 70% and up to 100% of the antioxidant compounds of interest. Thus, in the various embodiments as disclosed herein, the amount of an antioxidant compound of interest present in inventive compositions can be determined as the product of the weight percent of the extract reagent used in the formulation and the percentage of the antioxidant compound of interest in the selected reagent.

*Silybum Marianum* extract (containing Silymarin) is extracted from the fruit of the milk thistle plant (*Silybum Marianum*) and contains substantially three flavonoids of the flavonol subclass: silybin, which is predominant, the silydianin and the silychristin. Silymarin is known to have hepatoprotecting and depurating properties and it is used as adjuvant in the treatment of the liver damage.

*Origanum Vulgare* leaf extract (containing Origa'light) is extracted from oregano leaves. It is rich in hydroxycinnamic polyphenols, and has been shown to have lightening and antioxidant properties, and demonstrates good photostability.

*Coptis Chinensis* root extract has been used in traditional Chinese medicine for over two thousand years. It contains alkaloids, such as berberine, as well as coptisine, and has been demonstrated to have biologically beneficial effects including as an antioxidant.

*Scutellaria Baicalensis* root extract includes the compound baicalin, which has also been identified as a component of Chinese medicinal herb Huang-chin, is a flavone, a type of flavonoid. It is a potent antioxidant that demonstrates potent effects against oxidative stress diseases, inflammation, allergy, cancer, bacterial infections, etc.

In accordance with the disclosure, the amount of baicalin present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

Also in accordance with the disclosure, the amount of each of the at least one additional phenolic compounds and, in particular, of *Silybum Marianum* extract, *Origanum Vulgare* leaf extract, and *Coptis Chinensis* root Extract present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

Also in accordance with the disclosure, Vitamin E is present in the compositions from about 0.01% to about 20%; about 0.01% to about 10%; about 0.01% to about 1%; about 0.1% to about 5%; about 0.1% to about 1%; or about 0.5% to about 5%, based on the total weight of the composition.

Thus, in various embodiments, any one of the foregoing components selected from baicalin, *Silybum Marianum* extract, *Origanum Vulgare* leaf extract, *Coptis Chinensis* root extract and Vitamin E is present in a composition according to the disclosure in a weight percent amount from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to about 20 percent by weight, including increments and ranges therein and there between.

Further, in various embodiments, any one of the specific antioxidant components, such as baicalin or berberine, obtained as an extract, for example, *Scutellaria Baicalensis* root extract or *Coptis Chinensis* root extract, may be present in an composition according to the disclosure in a weight percent amount that is determined as the product of the percentage purity of the antioxidant in the extract and the percentage of the extract used in the formulation, for example, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to about 20 percent by weight, including increments and ranges therein and there between.

Optional Additional Antioxidants

The compositions can also contain one or more additional antioxidants that is/are different from the flavonoid(s) used in the composition and ferulic acid. Additional antioxidants can be any antioxidant suitable for use in cosmetic formulations. Suitable antioxidants include, but are not limited to, vitamin C, resveratrol, tannic acid, polyphenols, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as Vitamin E), vitamin A, co-enzyme Q10, bioflavonoids, glutathione, plant extracts (such as rosemary extract, olive leaf extracts), and green tea extracts. In another example of an antioxidant that is suitable for use is ferulic acid, which is a hydroxycinnamic acid that can be broadly found in giant fennel, the seeds of coffee, apple, artichoke, peanut, and orange, as well as in both seeds and cell walls of commelinid plants (such as rice, wheat, oats, and pineapple). Like many natural phenols, it is a strong antioxidant that is very reactive toward free radicals and reduces oxidative stress. Many studies suggest that ferulic acid may have antitumor activity.

The amount of additional antioxidants present in the compositions can range from about 0.01% to about 20%; about 0.1% to about 20%; or about 0.01% to about 10%, based on the total weight of the composition.

Optional Hydrotropes

Hydrotropes or glycols may be used in some embodiments to increase solubility of the components of the compositions if solubility of any of the components in water is low. A hydrotrope solution is prepared by completely dissolving one or more hydrotropic agents into water. The component(s) are then added in and mixed using stirring bar or any other mixer. Solubilization of the components occurs within minutes, and mixing continued until clear stable solution is obtained, usually within one hour of mixing. No heat is necessary by following this procedure to dissolve phenolic compounds. Everything is prepared at room temperature to keep the stability of phenolic compounds. This is extremely useful to protect the activity of certain compounds and also makes the process much easier.

Hydrotropes (or hydrotropic agents) are a diverse class of water-soluble compounds that are characterized by an amphiphilic molecular structure and ability to dramatically increase the solubility of poorly soluble organic molecules in water. The at least one hydrotrope is present in the composition in amounts effective to increase the solubility of the phenolic compound in water. At least one hydrotrope refers to one or a combination of two or more hydrotropes. One or a combination of two or more hydrotropes can be used to improve the solubility of phenolic compounds in water. The amount of hydrotrope will vary depending on the hydrotrope and the type and amount of phenolic compound. Increasing the water solubility of the phenolic compound(s) refers to increasing the solubility of the phenolic compound(s) in water in comparison with solubility of the phenolic compound(s) in water in the absence of the hydrotrope or hydrotropes.

An advantage of using hydrotropes is, once a stable solution is obtained, further dilution doesn't influence the stability of the solution. This is very different from organic solvents that are commonly used to increase the water solubility of phenolic compounds, such as polyphenols. Typically, an aqueous dilution of organic solvents with pre-dissolved phenolic compound(s), such as a polyphenol, results in crystallization or precipitation.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently, their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, nicotinamide (vitamin B3), caffeine, sodium PCA (sodium salt of pyrrolidone carbonic acid), sodium salicylate, urea, and hydroxyethyl urea. The suitability of a hydrotrope for use in cosmetic compositions can be determined using tests known in the art for determining effects on skin, and toxicity to humans.

The amount of hydrotropes present in the compositions can range from about 0.1% to about 20%; about 0.1% to about 10%; or about 1% to about 50%, based on the total weight of the composition.

Optional Additives

The compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, mineral or synthetic oils, gelling agents, antioxidants, solvents, fragrances, fillers, screening agents, odor absorbers and coloring materials.

These additives can be present in the composition according to the invention in proportions which are not limited, but which advantageously fall in the range from 0 to 50% by weight, or 1 to 50% by weight, with respect to the total weight of the composition.

Water

The compositions comprise from about 1 to about 99.9% by weight of water, with respect to the total weight of the composition. The amount of water in the composition can range from about 1 to 99.5%; about 1 to 60%; or about 1 to 50%, based on the total weight of the composition.

The pH of the compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Formulations Comprising the Compositions

Generally, any composition of the invention can be ingested, injected or topically applied to the skin (over any cutaneous region of the body) or to the mucous membranes (oral, jugal, gingival, genital, conjunctival, and the like). Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen and severe pruritus.

EXAMPLES

Example 1

TABLE 1

Oxygen Radical Absorbance Capacity of selected antioxidant compounds:

| Antioxidant | ORAC (µmolTolox/g) |
|---|---|
| baicalin | 4759 |
| Trolox (VitE) | 1000 |
| Silymarin | 1824 |
| Origa'light | 5125 |
| *Coptis chinensis* root extract | 2634 |
| Polydatin | 20159 |

Example 2

TABLE 2

Compositions of tested solution samples:

| Sample # | Antioxidant Association | AOX assay | Expected Value (µmolTolox/g) | Measured Value (µmolTrolox/g) | Increase % |
|---|---|---|---|---|---|
| 1 | 0.5% baicalin + 1% Vit E | ORAC | 34 | 36 | <10% |
| 2 | 0.5% baicalin + 1% Vit E + 0.5% silymarin | ORAC | 43 | 110 | 156% |
| 3 | 0.5% baicalin + 1% Vit E + 0.5% origa'light | ORAC | 59 | 89 | 51% |
| 4 | 0.5% baicalin + 1% Vit E + 0.5% *Coptis chinensis* root extract | ORAC | 47 | 76 | 62% |
| 5 | 0.5% baicalin + 1% Vit E + 1% Polydatin | ORAC | 259 | 293 | <15% |
| 6 | 0.5% baicalin + 1% Vit E + 3% Polydatin | ORAC | 662 | 704 | <10% |
| 7 | 0.5% Silymarin + 10% Vit C + 1% Vit E | ORAC | 465 | 363 | — |
| 8 | 1% Silymarin + 10% Vit C + 1% Vit E | ORAC | 474 | 407 | — |
| 9 | 0.5% Origa'light + 10% Vit C + 1% Vit E | ORAC | 481 | 403 | — |
| 10 | 0.5% Origa'light + 10% Vit C + 1% Vit E | ORAC | 507 | 433 | — |

The synergy was evident only in the specific combinations including a selected polyphenol, baicalin and Vitamin E. When the polyphenol selected from silymarin, origa'light, and *Coptis chinensis* root extract was removed or replaced by polydatin, or baicalin was replaced by Vitamin C, a synergistic effect was not observed.

Example 3: Inventive Serum Formulation with Inventive Compositions

TABLE 3

Serum

| Phase | INCI US | Inventive Sample 2 (wt %) | Inventive Sample 3 (wt %) | Inventive Sample 4 (wt %) |
|---|---|---|---|---|
| A | DIPROPYLENE GLYCOL | 10 | 10 | 10 |
| A | ALCOHOL DENAT. | 10 | 10 | 10 |
| A | PROPYLENE GLYCOL | 10 | 10 | 10 |
| A | *SILYBUM MARIANUM* EXTRACT (Silymarin) | | 0.5 | |
| A | TOCOPHEROL | 1 | 1 | 1 |
| B | WATER | 55 | 60 | 60 |
| B | NIACINAMIDE | 5 | 2 | 2 |
| B | CAFFEINE | 5 | 3 | 3 |
| B | *SCUTELLARIA BAICALENSIS* ROOT EXTRACT (baicalin) | 0.5 | 0.5 | 0.5 |
| B | *COPTIS CHINENSIS* ROOT EXTRACT | 0.5 | | |
| B | *ORIGANUM VULGARE* LEAF EXTRACT (Origa'light) | | | 0.5 |
| B | LAURETH-23 | 3 | 3 | 3 |

Serum Preparation:

Serum (simplex formulas that were tested in tubo directly).

Serum was prepared as follows. Phase A components were mixed at room temperature until clear solution was obtained. In a separate container, Phase B components were mixed at room temperature, with actives added after niacinamide and caffeine are completely dissolved in water. Phase B was then slightly heated at 65° C. to dissolve laureth-23. Then Phase A was added into Phase B and mixed for 30 minutes.

Example 4: Inventive Emulsion Formulations

The compositions according to the disclosure are suitable for integration broadly into different architectures, including, for example, emulsions such as oil-in-water (O/W), and water-in-oil (W/O) emulsions for cosmetic use.

Oil-in-Water Emulsion (Cream) Preparation

TABLE 4

Inventive O/W Cream Formulation

| Phase | INCI US Name | Concentration (wt %) |
|---|---|---|
| A | WATER | 66.65 |
| A | NIACINAMIDE | 2 |
| A | CAFFEINE | 3 |
| A | BAICALIN | 0.5 |
| A | GLYCERIN | 5 |
| A | PHENOXYETHANOL | 0.4 |
| A | SODIUM BENZOATE | 0.2 |
| A | DIPROPYLENE GLYCOL | 2 |
| B | DIMETHICONE | 3 |
| B | DIMETHICONE | 2 |
| B | BIS-PEG/PPG-20/20 DIMETHICONE | 0.5 |
| B | DIMETHICONE (and) DIMETHICONOL | 2 |
| B | DIMETHICONE (and) DIMETHICONE/VINYL DIMETHICONE CROSSPOLYMER | 0.5 |
| B | STEARETH-21 | 0.75 |
| B | NYLON-12 | 3 |
| C | POLYACRYLAMIDE (and) C13-14 ISOPARAFFIN (and) LAURETH-7 | 3 |
| D | BIOSACCHARIDE GUM-1 | 2 |
| E | TOCOPHEROL | 1 |
| G | ALCOHOL DENAT. | 2 |
| G | SILYMARIN | 0.5 |

Oil-in-water emulsion (cream) Preparation was prepared as follows. Phase A components were mixed at room temperature by sequential addition to water until a clear solution was obtained. In a separate container, Phase B components were mixed at room temperature until uniform. Phase B was then added into Phase A with homogenization at room temperature until uniform. Phase C was then added to the A/B homogenate and mixing continued at room temperature. Phase D, E and G were then added sequentially with continued mixing until a uniform texture was achieved.

Water-in-Oil Inverse Emulsion Preparation:

TABLE 5

Inventive W/O Emulsion Formulation

| Phase | INCI US Name | Concentration (wt %) |
|---|---|---|
| A | DIMETHICONE | 15.5 |
| A | DIMETHICONE (and) PEG/PPG-18/18 DIMETHICONE | 7 |
| B | WATER | 45.4 |
| B | DISODIUM EDTA | 0.1 |
| B | SODIUM CHLORIDE | 2 |
| B | NIACINAMIDE | 2 |
| B | CAFFEINE | 3 |
| B | BAICALIN | 0.5 |
| B | GLYCERIN | 3 |
| C | PROPYLENE GLYCOL | 9 |
| C | DIPROPYLENE GLYCOL | 7 |

TABLE 5-continued

Inventive W/O Emulsion Formulation

| Phase | INCI US Name | Concentration (wt %) |
|---|---|---|
| C | SILYMARIN | 0.5 |
| C | ALCOHOL DENAT. | 5 |

Water-in-oil emulsion Preparation was prepared as follows. Phase A components were mixed at room temperature. In a separate container, Phase B components were mixed at room temperature by sequential addition to water until a clear solution was obtained. Phase B was then added into Phase A with homogenization at room temperature until uniform. In a separate container, Phase C was mixed at room temperature or with slight heating as needed to achieve a clear solution. Phase C was then added to the A/B homogenate and homogenization continued at room temperature until a uniform texture was achieved.

Compositions and formulations as described in the representative embodiment's herein included commercially available materials, including, for example: *Coptis Chinensis* root extract from CHENGDU WAGOTT PHARMACEUTICAL; Berberin HCl 98% from Jiahe; Silymarin from MMP; Silymarin from Guilin Layn Natural Ingredients; Origa'light from BERKEM; baicalin from MMP; and, TOCOPHEROL (Vitamin E) from DSM.

What is claimed is:

1. An antioxidant composition comprising:
   (a) about 0.01% to about 20% of at least one polyphenol selected from the group consisting of *Silybum Marianum* extract, *Origanum Vulgare* leaf extract, and *Coptis Chinensis* root extract;
   (b) about 0.01% to about 20% of baicalin; and
   (c) about 0.01% to about 20% of Vitamin E;
   wherein all amounts are percentages by weight based on the total weight of the composition; and wherein amounts of said selected polyphenol (a), and baicalin (b) and Vitamin E (c) are selected to produce a synergistic antioxidant activity that is at least 25% greater than a sum of the antioxidant activity for each of said selected polyphenol (a), baicalin (b) and Vitamin E (c).

2. A composition according to claim 1, wherein said at least one polyphenol (a) is *Silybum Marianum* extract.

3. A composition according to claim 1, wherein said at least one polyphenol (a) is *Origanum Vulgare* leaf extract.

4. A composition according to claim 1, wherein said at least one polyphenol (a) is *Coptis Chinensis* root extract.

5. A composition according to claim 1, wherein said composition is appropriate for topical application to the skin and is in the form of a lotion, serum, gel, milk, foam, liquid foundation or cream.

6. A composition according to claim 1 further comprising (d) at least one additional antioxidant different than (a)-(c).

7. A composition according to claim 1 further comprising at least one hydrotrope.

8. A composition according to claim 7 wherein said hydrotrope is caffeine or nicotinamide.

9. A composition according to claim 1 wherein the at least one polyphenol is present in an amount from about 0.01% to about 10% by weight based on the total weight of the composition.

10. A composition according to claim 1 wherein the at least one polyphenol is present in an amount from about 0.01% to about 5% by weight based on the total weight of the composition.

11. A composition according to claim 1 wherein baicalin is present in an amount from about 0.01% to about 10% by weight based on the total weight of the composition.

12. A composition according to claim 1 wherein baicalin is present in an amount from about 0.01% to about 5% by weight based on the total weight of the composition.

13. A composition according to claim 1 wherein Vitamin E is present in an amount from about 0.01% to about 10% by weight based on the total weight of the composition.

14. A composition according to claim 1 wherein Vitamin E is present in an amount from about 0.01% to about 5% by weight based on the total weight of the composition.

15. A composition according to claim 7 wherein the hydrotrope is present in an amount from about 0.01% to about 20% by weight based on the total weight of the composition.

16. An antioxidant composition comprising:
(a) at least one polyphenol selected from the group consisting of *Silybum Marianum* extract, *Origanum Vulgare* leaf extract, and *Coptis Chinensis* root extract;
(b) baicalin; and
(c) Vitamin E;
wherein amounts of said selected polyphenol (a), and baicalin (b) and Vitamin E (c) are selected to produce a synergistic antioxidant activity that is at least 25% greater than a sum of the antioxidant activity for each of said selected polyphenol (a), baicalin (b) and Vitamin E (c).

17. A composition according to claim 16, comprising
(a) about 0.5% of at least one polyphenol selected from the group consisting of *Silybum Marianum* extract, *Origanum Vulgare* leaf extract, and *Coptis Chinensis* root extract;
(b) about 0.5% of baicalin; and
(c) about 1% of Vitamin E;
wherein all amounts are percentages by weight based on the total weight of the composition and wherein amounts of said selected polyphenol (a), and baicalin (b) and Vitamin E (c) are present in amounts selected to produce a synergistic antioxidant activity that is at least 25% greater than a sum of the antioxidant activity for each of said selected polyphenol (a), baicalin (b) and Vitamin E (c).

18. A method for preparing an antioxidant composition comprising: including in said composition at least one polyphenol (a), and baicalin (b) and Vitamin E (c), wherein amounts of said polyphenol (a), and baicalin (b) and Vitamin E (c) are present in amounts selected to produce a synergistic antioxidant activity that is at least 25% greater than a sum of the antioxidant activity for each of said selected polyphenol (a), baicalin (b) and Vitamin E (c).

19. A method according to claim 18, further comprising: including in said composition (d) one or more additional antioxidants different than (a)-(c), and a hydrotrope (e).

20. The method for preparing a cosmetic formulation comprising an antioxidant composition, comprising: including in said formulation a composition according to claim 1, and further including one or more cosmetically acceptable components for forming one of an aqueous serum, an oil-in-water emulsion, and a water-in-oil emulsion.

* * * * *